United States Patent
Schweikert et al.

(10) Patent No.: US 8,052,646 B2
(45) Date of Patent: Nov. 8, 2011

(54) RELEASABLY LOCKING DILATOR AND SHEATH ASSEMBLY

(75) Inventors: Timothy Schweikert, Levittown, PA (US); Mahase Nardeo, Collegeville, PA (US)

(73) Assignee: Medical Components, Inc., Harleysville, PA (US)

( * ) Notice: Subject to any disclaimer, the term of this patent is extended or adjusted under 35 U.S.C. 154(b) by 798 days.

(21) Appl. No.: 12/165,896

(22) Filed: Jul. 1, 2008

(65) Prior Publication Data

US 2008/0300538 A1 Dec. 4, 2008

Related U.S. Application Data

(60) Division of application No. 10/949,614, filed on Sep. 24, 2004, now Pat. No. 7,422,571, which is a continuation-in-part of application No. 10/651,114, filed on Aug. 28, 2003, now Pat. No. 6,796,991.

(60) Provisional application No. 60/406,740, filed on Aug. 29, 2002.

(51) Int. Cl.
*A61M 5/178* (2006.01)

(52) U.S. Cl. .................................. 604/167.04; 604/264

(58) Field of Classification Search .................. 604/161, 604/164.1, 167.01–167, 264; 606/108, 191, 606/198, 184–187; 600/184–200
See application file for complete search history.

(56) References Cited

U.S. PATENT DOCUMENTS

| | | |
|---|---|---|
| 4,475,548 A | 10/1984 | Muto |
| 4,865,593 A | 9/1989 | Ogawa et al. |
| 5,125,904 A | 6/1992 | Lee |
| 5,207,649 A | 5/1993 | Aruny |
| 5,250,033 A | 10/1993 | Evans et al. |
| 5,304,142 A | 4/1994 | Liebl et al. |
| 5,312,355 A | 5/1994 | Lee |
| 5,350,363 A | 9/1994 | Goode et al. |

(Continued)

FOREIGN PATENT DOCUMENTS

EP 631793 1/1995

(Continued)

OTHER PUBLICATIONS

Supplementary Partial European Search Report dated Dec. 8, 2008; EP 1791591 (10 pages).

(Continued)

*Primary Examiner* — Kevin T Troung
(74) *Attorney, Agent, or Firm* — Fox Rothschild LLP

(57) ABSTRACT

A releasably locking dilator and sheath assembly and methods for releasing the dilator from the sheath and longitudinally splitting the sheath are provided. The assembly includes a dilator having a dilator hub and a sheath having a sheath hub. The sheath hub has a valve and two opposing winged tabs, each tab having a perpendicular portion and an angled portion as well as a female threaded portion. The dilator hub has a male threaded portion designed to engage the female threaded portion of the sheath hub. The dilator is released from the sheath by rotating the dilator 90° in relation to the sheath and pulling the dilator out of the sheath. The sheath is longitudinally split by creating a couple on each of the winged tabs thereby forcing the sheath and the sheath hub to split longitudinally. With the sheath and sheath hub split longitudinally, the sheath is removed from around a catheter while leaving the catheter in place.

22 Claims, 10 Drawing Sheets

U.S. PATENT DOCUMENTS

| | | | |
|---|---|---|---|
| 5,423,762 A | 6/1995 | Hillstead | |
| 5,441,504 A | 8/1995 | Pohndorf et al. | |
| 5,613,953 A | 3/1997 | Pohndorf | |
| 5,755,693 A | 5/1998 | Walker et al. | |
| 5,782,807 A | 7/1998 | Falvai et al. | |
| 5,885,217 A | 3/1999 | Gisselberg et al. | |
| 6,083,207 A | 7/2000 | Heck | |
| 6,197,016 B1 | 3/2001 | Fourkas et al. | |
| 6,322,541 B2 | 11/2001 | West et al. | |
| 6,336,914 B1 | 1/2002 | Gillespie, III | |
| 6,562,049 B1 | 5/2003 | Norlander et al. | |
| 6,712,791 B2 | 3/2004 | Lui et al. | |
| 6,764,464 B2 | 7/2004 | McGuckin, Jr. et al. | |
| 6,796,991 B2 * | 9/2004 | Nardeo | 606/191 |
| 6,808,509 B1 | 10/2004 | Davey | |
| 6,808,520 B1 | 10/2004 | Fourkas et al. | |
| 6,966,896 B2 | 11/2005 | Kurth et al. | |
| 7,101,353 B2 * | 9/2006 | Lui et al. | 604/164.05 |
| 2001/0049499 A1 | 12/2001 | Lui et al. | |
| 2003/0050604 A1 | 3/2003 | Lui et al. | |
| 2003/0088264 A1* | 5/2003 | Spohn et al. | 606/194 |
| 2004/0102738 A1 | 5/2004 | Dikeman et al. | |
| 2004/0267202 A1 | 12/2004 | Potter | |
| 2005/0010238 A1 | 1/2005 | Potter et al. | |
| 2005/0027257 A1 * | 2/2005 | Davey | 604/167.03 |
| 2006/0030817 A1 | 2/2006 | Kraus et al. | |

FOREIGN PATENT DOCUMENTS

| | | |
|---|---|---|
| JP | H03-5443 U | 1/1991 |
| JP | H 05-115555 A | 5/1993 |
| JP | 6502797 | 3/1994 |
| WO | 9320879 | 10/1993 |
| WO | 95/13840 | 5/1995 |
| WO | WO 00/64527 A | 11/2000 |
| WO | 2005/107843 | 11/2005 |

OTHER PUBLICATIONS

Office Action dated Jun. 29, 2010; corresponding JP Application No. 2007-533582 (cover—1 page; office action—4 pages; translation—5 pages).

Written Opinion dated Jul. 18, 2011; PCT/US2005/033612 (7 pages).

Office Action, Corresponding to parent application Japanese Application No. 2004-531,626 (three pages).

Intl Search Report, May 4, 2006 from PC/US05/33612 (4 pages).

Written Opinion dated May 4, 2006 from PCT/US05/33612 (5 pages).

* cited by examiner

RELEASABLY LOCKING DILATOR AND SHEATH ASSEMBLY

CROSS REFERENCE TO RELATED APPLICATIONS

The present application is a Divisional of U.S. patent application Ser. No. 10/949,614 filed Sep. 24, 2004 now U.S. Pat. No. 7,422,571, in turn a Continuation in Part of U.S. patent application Ser. No. 10/651,114 filed on Aug. 28, 2003 now U.S. Pat. No. 6,796,991, which claims the benefit of U.S. Provisional Patent Application Ser. No. 60/406,740 filed on Aug. 29, 2002. The text of U.S. patent application Ser. No. 10/651,114 filed on Aug. 28, 2003 and U.S. Provisional Patent Application Ser. No. 60/406,740 filed on Aug. 29, 2002 are both incorporated herein by reference.

FIELD OF THE INVENTION

This invention relates to invasive medical devices which aid in the catheterization of human blood vessels. In particular, this invention relates to a releasably locking dilator and tear away sheath assembly, which is used to enlarge an opening in a patient's blood vessel during insertion of a catheter into the blood vessel and then guide the catheter into the blood vessel to be catheterized.

BACKGROUND OF THE INVENTION

Catheters are used in numerous medical procedures. In particular, catheters are used for the introduction or removal of fluids from various venous regions and vessels throughout the body, such as for hemodialysis. The procedure by which these catheters are introduced to the body is delicate and complex. One particularly intricate challenge to catheterization is enlarging a hole in the flesh and vessel to be catheterized while minimizing blood loss and trauma to the patient.

Generally, to insert any catheter in a blood vessel, the vessel is identified by aspiration with a long hollow needle in accordance with the Seldinger technique. When blood enters a syringe attached to the needle, indicating that the vessel has been found, a thin guide wire is then introduced, typically through the syringe needle or other introducer device, into the interior of the vessel. The introducer device is then removed, leaving the guide wire within the vessel. The guide wire projects beyond the surface of the skin.

At this point, several options are available to a physician for catheter placement. The simplest option is to pass a catheter into the vessel directly over the guide wire. The guide wire is then removed. However, use of this technique is only possible in cases where the catheter is of a relatively small diameter, made of a stiff material and not significantly larger than the guide wire. If, however, the catheter is of a relatively large diameter and/or not made of a soft material, one preferable method of inserting the catheter into the vessel is through an introducer sheath. The introducer sheath is simply a large, stiff, thin-walled tube, which serves as a temporary conduit for the catheter that is being placed. The sheath is positioned by placing a dilator, which has a hollow passageway along its longitudinal axis, inside of the sheath and passing both the dilator and the sheath together into the vessel over the guide wire. The dilator expands the opening in the blood vessel to allow for catheter insertion into the vessel. The guide wire and dilator are then removed, leaving the thin-walled sheath in place. The catheter is then inserted into the vessel through the sheath.

In a setting where a catheter with a hub or other attachment at the proximal end of the catheter has a feature which is larger than that of the inner diameter of the sheath, it is necessary to have a tear-away sheath that can be split away from the catheter as the sheath is being removed from the patient. By splitting the sheath along its longitudinal axis as the sheath is being removed from the patient, the inserting physician will be able to pull out the sheath in such a way that the portion removed from the patient is split, thereby not interfering with any encumbrances on the catheter. Generally, tear away sheaths are manufactured in a way that aids in the tearing of the sheath at two opposing points on the circumference of the sheath, thereby splitting the sheath into two halves separated longitudinally through the center of the sheath.

A sheath is generally constructed with a hub at its proximal end. This hub serves as a handle, a mating point for a dilator, and a flat surface to aid in the prevention of blood loss or contamination. When a sheath needs to be split apart in order to be successfully withdrawn from the body while leaving the catheter in place, the hub will also have to be split apart in order to clear the catheter. Preferably, the hub will split along the same lines as the sheath. To accomplish this, the hub must be designed with reveals or other weaknesses along two longitudinal lines aligned with the weaknesses in the sheath. Some previous examples of these weaknesses are tabs or webs which connect two halves of the hub, or recesses in the material comprising the hub. The weaknesses in the hub will help the inserting physician to break apart the hub in line with the tear seams on the sheath.

Another important facet of the hub is a set of tabs that protrude from the center. These tabs not only help the inserting physician to align, insert and withdraw the sheath, but also to pull the sheath so that the sheath can be removed from around a catheter while still leaving the catheter in place. There are a number of different tab configurations, but it is important to have one which allows for easy maneuverability, control, and leverage. One design includes a hub wherein the tabs protrude from the hub perpendicular to a plane which includes the tear seams in the sheath and the longitudinal axis of the sheath. In this design, the tabs are diametrically opposed from each other and are spaced in such a way that when the tabs are grasped and pulled apart from each other, the sheath and its hub will split down the middle. Another desirable feature of the tabs is that the tabs provide leverage for breaking apart the hub in a manner that does not cause trauma to the incision in the body.

During insertion, especially in the time between the removal of the dilator from the sheath and the insertion of the catheter through the sheath, it is possible for blood loss through the sheath, or the introduction of contaminants or air through the sheath and into the vessel. For this reason, it is desirable that measures be taken to prevent blood, air or contaminants from traveling through the sheath. In the past, inserting physicians have simply held their thumb over the opening in the proximal end of the sheath; however, a more permanent and reliable means for preventing blood, air or contaminants from traveling through the sheath is desirable. It is therefore desirable for the hub to include a valve located in the sheath. Such a valve would facilitate the insertion of objects such as a catheter, dilator or syringe through the sheath while restricting blood loss and reducing the chance of contaminants entering the patient's bloodstream when the sheath is not engaged with a dilator or a catheter.

In the case where a sheath does not have a small diameter or a narrow point, the dilator is often used to aid in the insertion of the sheath. The dilator has a long tubular section, the outside diameter of which is slightly smaller than the inside diameter of the sheath. The dilator also has a pointed tip on its distal end and a hollow center, which runs along the entire length of the dilator. The dilator is inserted into the body with the guidewire running through its center, thereby allowing the tip of the dilator to follow the guidewire to the place that is to be catheterized. On its proximal end, the dilator may have a hub. Like the hub of the sheath, this hub can also serve a number of purposes, such as providing a stable handle to aid in guiding the dilator into the vein, and as a mechanism which can mate with the sheath hub to form a locked connection.

Some dilator and sheath assemblies that include a connection between the dilator and sheath are known. U.S. Pat. No. 5,885,217 to Gisselberg et al. discloses a dilator and sheath assembly, wherein the dilator and sheath are held together by locking tabs which provide a stop to hold the dilator in place during insertion. However, in this configuration, the dilator may rotate about its longitudinal axis in relation to the sheath, thereby inadvertently and prematurely disengaging the dilator from the sheath. U.S. Pat. No. 5,098,392 to Fleischhacker et al. discloses a dilator and sheath assembly, wherein the dilator is attached to the sheath through a clamp wherein the clamp is part of the dilator hub. However, this design presents the ability to come unclamped leading to the dilator backing out of the sheath. U.S. Pat. No. 4,772,266 to Groshong discloses a dilator and sheath assembly, wherein the hubs of the dilator and the sheath lock together by means of compression. However, it would be possible for the dilator to back out of the sheath in this configuration if excessive force is exerted on the tip of the dilator.

It would be beneficial to provide a dilator and sheath assembly that incorporates a stable releasably locking mechanism to prevent the dilator from backing out of the sheath longitudinally during insertion which is not prone to coming unlocked or releasing during use. It would also be beneficial for the sheath of the dilator and sheath assembly to have a means for sealing the passageway to the patient's vessel, thereby restricting blood loss and reducing the introduction of contaminants into the bloodstream. Moreover, it would be beneficial for this type of mechanism to have handles, which allow the inserting physician to gain leverage in the process of splitting the sheath apart.

BRIEF SUMMARY OF THE INVENTION

Briefly, the present invention provides a releasably locking dilator and sheath assembly and methods for releasing the dilator from the sheath and longitudinally splitting the sheath in the course of inserting a catheter into a desired vessel to be catheterized.

The invention provides a releasably locking dilator and sheath assembly, comprising a dilator and a sheath. The dilator has a distal tip, an elongated dilator stem, a proximal dilator end, and a dilator hub fixedly connected to the proximal dilator end. The dilator hub includes a threaded portion on its distal end. The sheath comprises a distal end, an elongated hollow tubular section, a proximal sheath end, and a sheath hub fixedly connected to the proximal sheath end. The sheath also comprises a longitudinal axis extending between the proximal sheath end and the distal sheath end as well as at least one tear seam disposed longitudinally on the sheath surface. The sheath hub includes a proximal portion, a mating threaded portion at a proximal end thereof and a valve. The threaded portion of the dilator hub and the mating threaded portion of the sheath hub provide a releasably locking engagement between the dilator and the sheath. The sheath is sized to frictionally retain the dilator.

The invention further provides a releasably locking dilator and sheath assembly, wherein the dilator comprises an elongated dilator stem having a proximal end and a dilator hub fixedly connected to the proximal dilator end. In addition, the sheath comprises an elongated tubular portion having a longitudinal axis, a proximal sheath end a distal sheath end, and a valve located at the proximal sheath end. The tubular portion of the sheath is sized to frictionally retain the dilator stem. The sheath also comprises at least one tear seam extending between the proximal sheath end and the distal sheath end and a sheath hub fixedly connected to the proximal sheath end. The dilator and sheath assembly comprises a means for providing a releasably locking engagement between the distal portion of the sheath hub and the proximal portion of the dilator hub.

The invention further comprises a releasably locking dilator and sheath assembly, wherein the dilator comprises an elongated dilator stem, a proximal dilator end and a dilator hub having a threaded portion on its distal end fixedly connected to the proximal dilator end. The sheath includes an elongated tubular portion having a proximal sheath end, a distal sheath end and a longitudinal axis extending between the proximal sheath end and the distal sheath end. The assembly includes a valve disposed at the proximal sheath end. The sheath further comprises two tear seams extending along the tubular portion between the proximal sheath end and the distal sheath end, wherein the two tear seams are located on opposite sides of the sheath and are coplanar with the longitudinal axis of the sheath. The sheath further comprises a first and second sheath hub portions, each of which comprise an inverted semicircular edge fixedly connected to the sheath. The first and second sheath hub portions generally encircle the tubular sheath, with spaces between the first and second sheath hub portions. The first and second sheath hub portions comprise a first and second threaded portion, respectively, at a proximal end thereof. The first and second threaded portions combined comprise a circular threaded portion forming the proximal end of the sheath which is matable with the threaded portion of the dilator hub to provide a releasably locking engagement between the dilator and the sheath.

The invention further provides a method of separating a dilator from a sheath. The method includes providing a dilator having a dilator stem extending along a longitudinal axis and a dilator hub connected to a proximal end of the dilator stem, wherein the dilator hub comprises a male threaded portion. The method also includes providing a sheath having a sheath hub comprising a valve, a female threaded portion and winged tabs having a perpendicular portion and an angular portion whereby the dilator is releasably connected to a sheath by mating the threads on the dilator hub to the threads on the sheath hub. The method further comprises rotating the dilator around the longitudinal axis in relation to the sheath, thereby unthreading the dilator and the sheath and disengaging the sheath.

The invention further comprises a method of removing a sheath from around a catheter assembly, wherein the catheter assembly and sheath are both partially disposed inside of a desired vessel to be catheterized. The sheath includes a longitudinal axis, a distal portion having a distal tip with a hollow portion aligned with the longitudinal axis of the sheath, an elongated tubular structure comprising a hollow passageway traversing the entire longitudinal axis of the sheath, a proximal portion having a proximal tip at its proximal end, a hollow passageway along the longitudinal axis of the sheath, and two opposing tear seams running the entire length of the sheath and coplanar with the longitudinal axis of the sheath. The sheath also includes a sheath hub fixedly connected to the proximal portion of the sheath. The sheath hub comprises a valve disposed at a proximal end of the sheath and two opposing reveals which run parallel to the longitudinal axis of the tubular sheath and are coplanar with the tear seams running along the surface of the sheath and the longitudinal axis of the sheath. The sheath hub also includes two opposing winged tabs; each tab includes a perpendicular portion and an angled portion. The perpendicular portion extends laterally from the sheath hub in a plane which is perpendicular to the plane containing the longitudinal axis of the sheath and the two opposing reveals. The angled portion of the tab extends from the perpendicular portion, wherein an angle between the proximal surface of the perpendicular portion and the angled portion is between 90° and 179°. The method further comprises applying a distal force to the proximal surface of the angled portion of each of the winged tabs; applying a proximal force to the distal surface of each of the tabs at a point on the tab closer to the center of the sheath than the point upon which the distal force is applied to the proximal surface; and grasping the tabs of the sheath and pulling them outward from the center of the sheath, thereby separating the sheath into two halves along the tear seams running the length of the sheath; and pulling the sheath in the proximal direction.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION OF THE INVENTION

Figure 1:
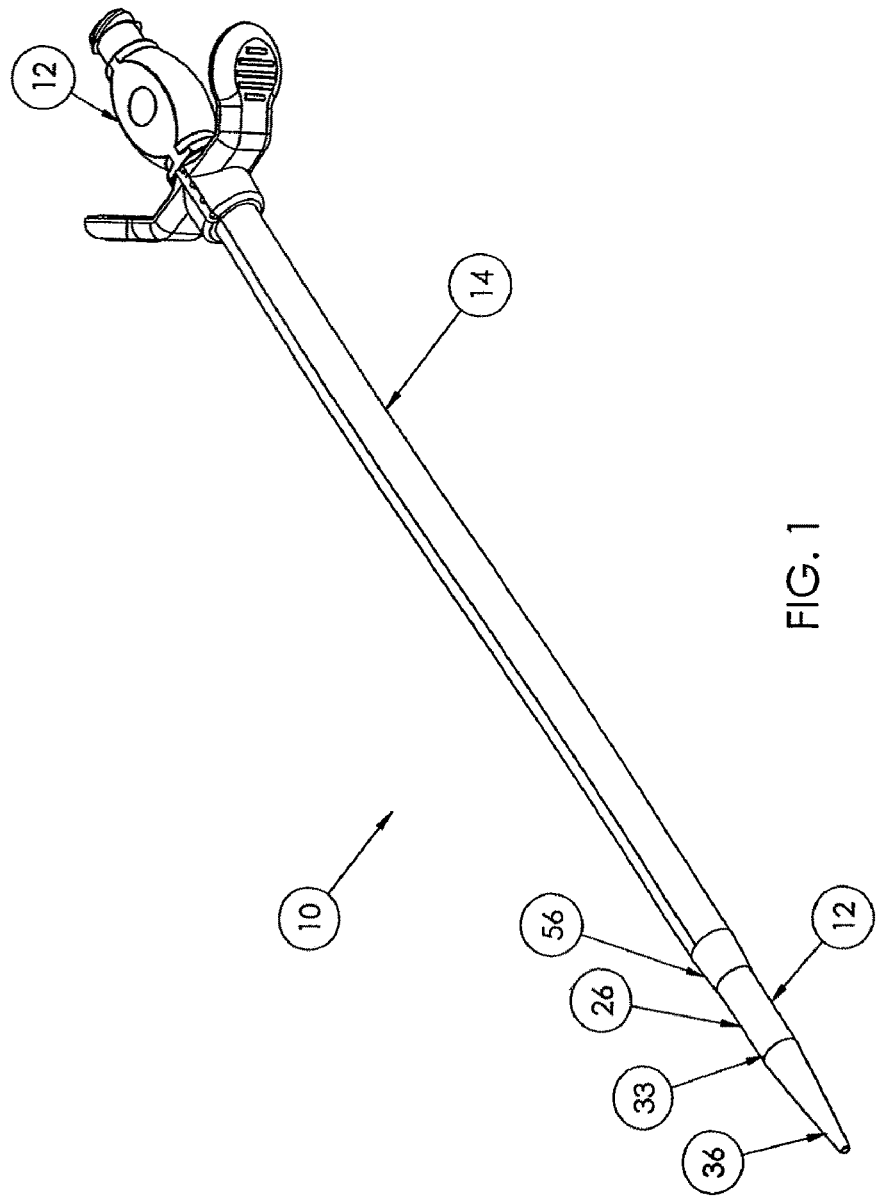
FIG. 1 is a perspective view of a releasably locking dilator and sheath assembly in a locked state in accordance with an embodiment of the present invention.

In the drawings, like numerals indicate like elements throughout. Certain terminology is used herein for convenience only and is not to be taken as a limitation on the present invention. The terms "distal" and "proximal" refer to the directions "away from" and "closer to," respectively, the body of the physician inserting the dilator and sheath assembly into a patient. The terminology includes the words above specifically mentioned, derivatives thereof, and words of similar import.

The following describes a preferred embodiment of the present invention. However, it should be understood, based on this disclosure, that the invention is not limited by the preferred embodiment described herein. Referring now to the drawings in detail, there is shown in FIG. 1, an embodiment of a releasably locking dilator and sheath assembly 10. As shown in throughout, the assembly includes a dilator 12 and a sheath 14, which are releasably locked to each other. The dilator 12 is longer than the sheath 14 so that the dilator 12, in the releasably locked position with the sheath 14, as shown in FIG. 1, passes through the sheath 14 so that a distal tip 36 of the dilator 12 extends beyond the distal end 56 of the sheath 14.

Figure 2:
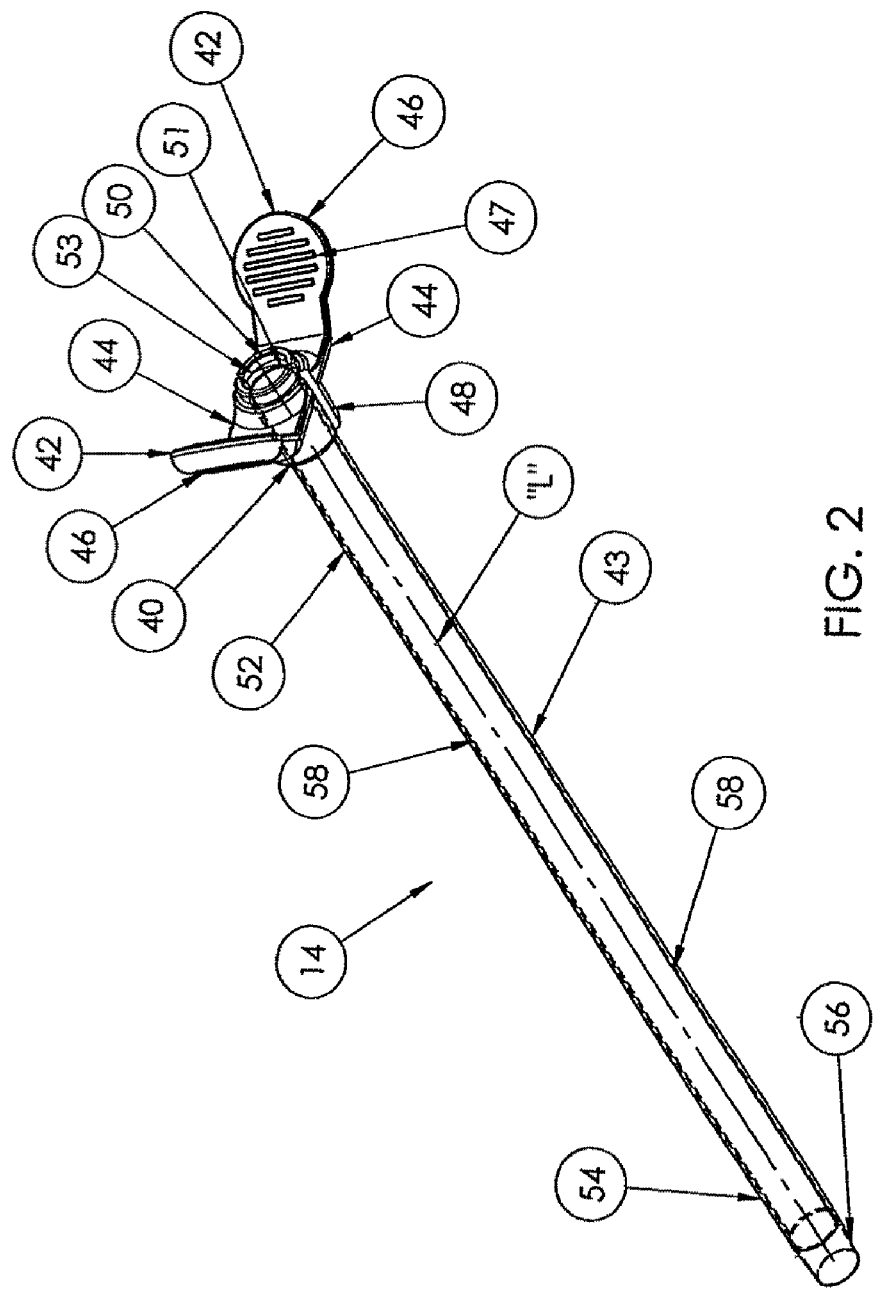
FIG. 2 is a perspective view of the sheath only, from FIG. 1.

The sheath 14, as shown in FIG. 2, is a device used to aid in the insertion of a catheter (not shown) into a vessel (not shown) to be catheterized, as is well known in the art. Since the sheath 14 is generally more rigid than a catheter, the sheath 14 can be maneuvered into place with less effort and trauma to the patient than a catheter. The catheter is then inserted into the vessel through the sheath 14. Once the catheter is in place, the sheath 14 may be removed, thereby leaving the catheter in its desired position. If the catheter has any encumbrance, such as a hub, on its proximal end, the sheath 14 will have to be split in order to remove it from the patient's body while leaving the catheter in place.

The sheath 14 includes a distal end 54 having a tapered distal tip 56, an elongated tubular portion 43, and proximal end containing a sheath hub 40. At least one tear seam 58 is longitudinally disposed along the entire length of the sheath 14. In this preferred embodiment, two tear seams 58 are present. These tear seams 58 are located on opposite sides of the sheath 14 so that a plane "P" containing the two tear seams 58 bisects the sheath 14 longitudinally. The plane "P" contains the longitudinal axis "L", as shown in FIG. 3, and extends from the line "L" perpendicular to the surface of the paper.

Figure 3:
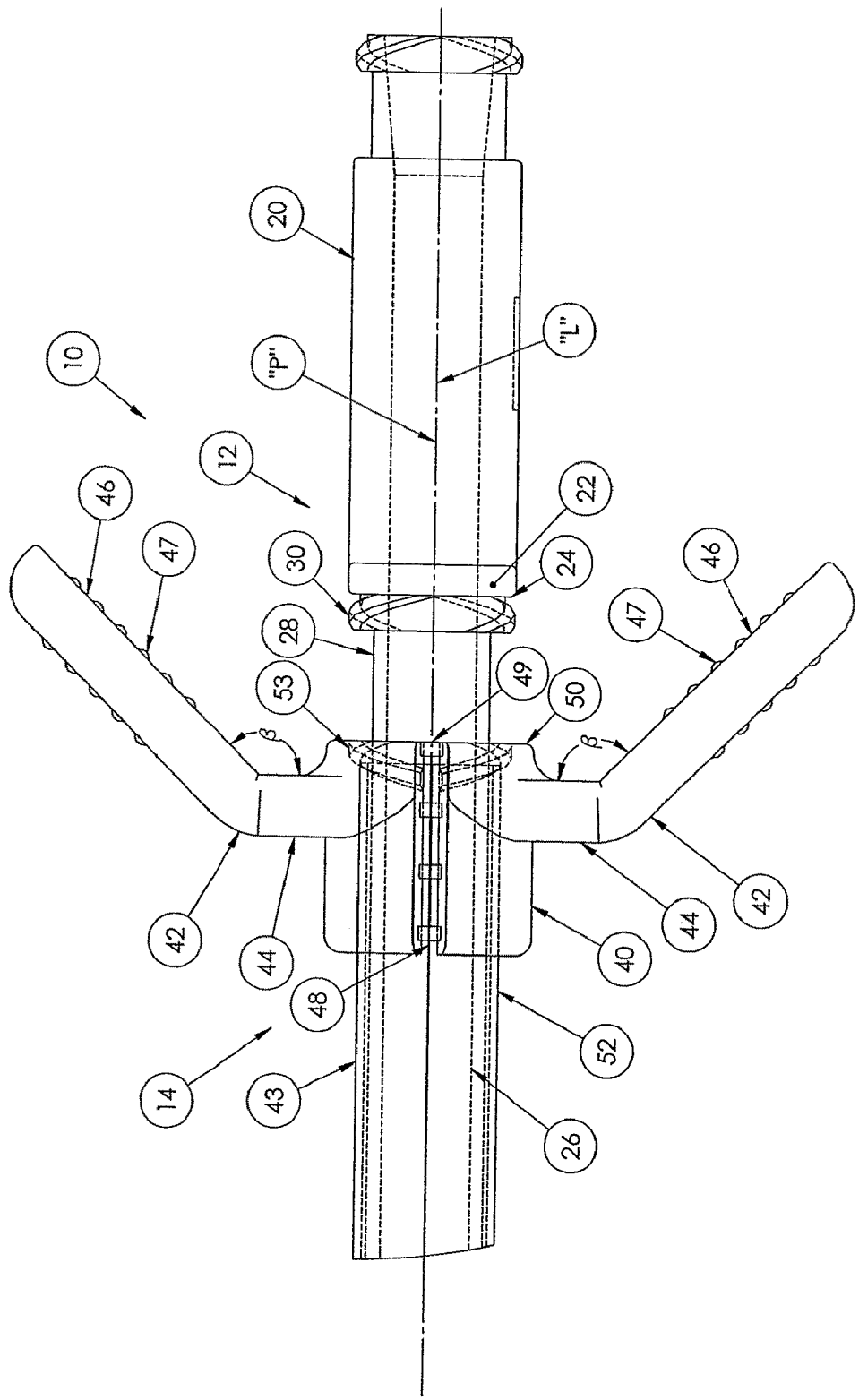
FIG. 3 is an enlarged top plan view, in cross-section, of the proximal end of the releasably locking dilator and sheath assembly in a released state.

Referring to FIGS. 2 and 3, two diametrically opposed reveals 48 are located on the sheath hub 40, along the tubular portion of the hub. Each reveal 48 is preferably aligned with one of the tear seams 58 of the sheath 14, so that the reveals 48 and the tear seams 58 are coplanar. At least one webbing member 49 is shown and optionally such a webbing member 49 may be disposed on both sides of sheath hub 40 at the proximal ends of reveals 48. The sheath hub 40 is fixedly connected to the proximal end 52 of the sheath 14 such as by an adhesive, ultrasonic bonding, insert molding or another method known to those skilled in the art. The longitudinal axis "L" extends through the sheath 14 and the sheath hub 40. The sheath hub 40 includes an elongated tubular portion surrounding a portion of the proximal end of the sheath, and first and second diametrically opposed winged tabs 42 extending from the sheath hub adjacent its proximal end; the first and second tabs 42 each include a perpendicular portion 44, perpendicular to the longitudinal axis "L" of the sheath 14, and an angled portion 46. The winged tabs 42 extend away from the plane that contains the diametrically opposed reveals 48 of the hub 40 and the tear seams 58 of the sheath 14. As shown in FIG. 3, an angle "β" extends between the proximal surface of the perpendicular portion 44 and the angled portion 46 of each of the wings 42. The angle "A" ranges from approximately 90° to approximately 179° Preferably, the angle "β" is between approximately 130° to approximately 140°; however, those skilled in the art will recognize that the angle "β" can have other ranges as well. The angled portions 46 of the winged tabs 42 include raised ridges 47 on their proximal surface to aid in gripping the tabs 46. Alternatively, other raised features on the winged tabs 42, such as bumps or a crosshatched pattern (not shown) may also assist the gripping the winged tabs 42.

As best seen in FIG. 3, the sheath hub 40 is fixedly connected to the proximal end 52 of the sheath 14 such that the exterior of the tubular portion 43 of the sheath 14 is fixedly connected to a portion of the inside of the sheath hub 40. Referring back to FIG. 2, the sheath hub 40 has an opening 51 and a top surface 50, which is generally flush around the entire circumference of the opening 51. The flush top surface 50 assists in preventing blood loss when the dilator 12 is removed from the sheath 14. The inserting physician may utilize the top surface 50 to prevent blood loss by placing a thumb over the entire opening 51 in the proximal end of the sheath hub 40, as is commonly done in the art. The opening 51 in the proximal end of the sheath hub 40 also serves as a proximal end to the sheath tubing 43. The part of the inner portion of the sheath hub 40 not fixedly connected to the sheath 14, may contain features that serve to mate the sheath 14 to the dilator 12 and form a releasably locking connection. The present embodiment shows a part of inner portion of the sheath hub 40 having female threads 53.

Figure 4:
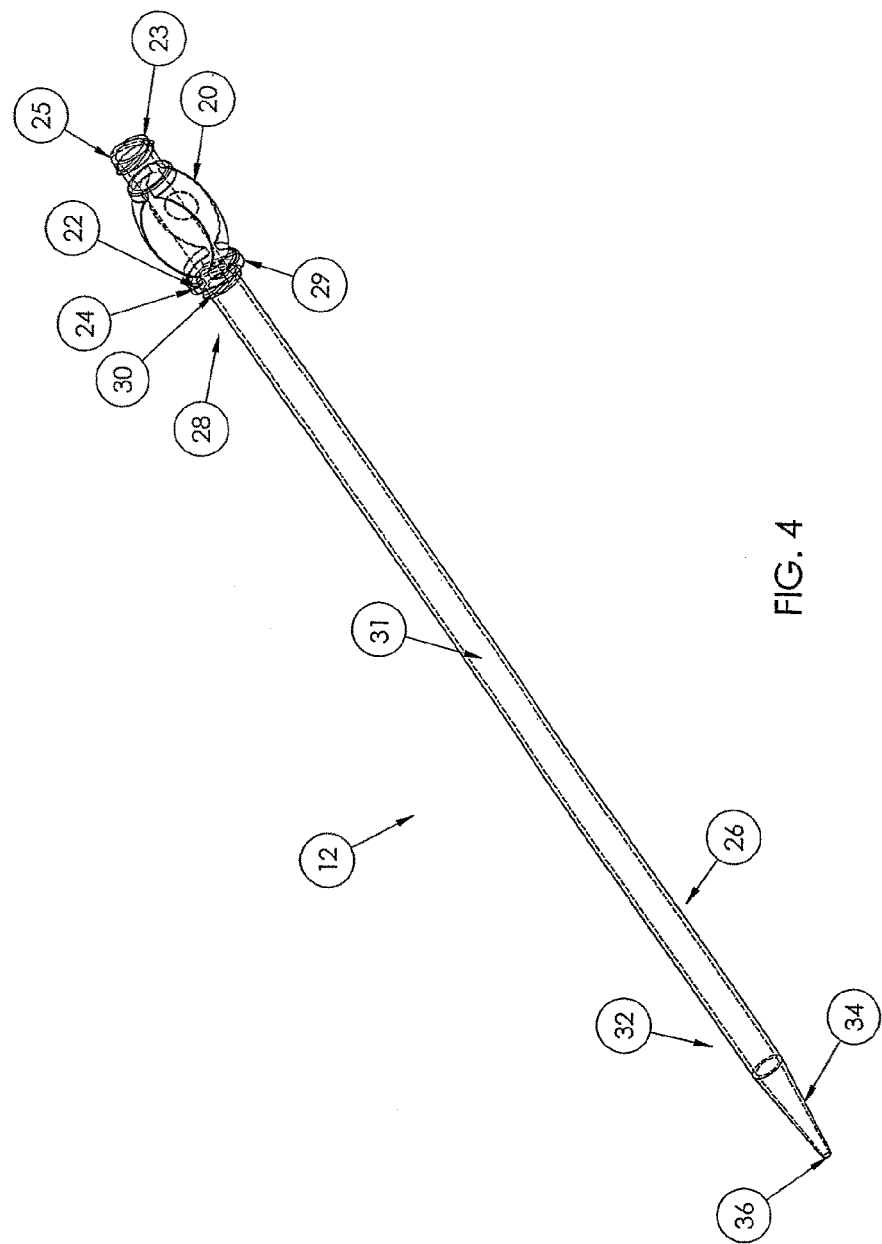
FIG. 4 is a perspective view of the dilator only, from FIG. 1.

Referring to FIG. 4, the dilator 12 is an elongated device that includes a proximal end 28, a distal end 32 and a stem 26 extending between the proximal end 28 and the distal end 32. At the distal end 32 of the dilator stem 26, a transition portion 34 reduces in diameter to a conically shaped distal tip 36. When in a releasably connected state with the dilator 12 inside of the sheath 14, the dilator 12 and sheath 14 share the same longitudinal axis "L". The exterior diameter of the stem 26 of the dilator 12 is sized to allow a slight frictional engagement between the inside of the sheath 14 and the outside of the dilator 12. This frictional engagement will serve to form a seal between the dilator 12 and the sheath 14 and reduce or prevent blood seepage through the sheath 14 while the dilator 12 and sheath 14 are releasably connected. Preferably, the dilator 12 includes a hollow passageway 31 along the length of the dilator 12 from the distal tip 36 to the proximal end of the dilator hub 23. The hollow passageway 31 allows the dilator 12 to be inserted over a guidewire (not shown) and follow the guidewire to the desired position inside the vessel to be catheterized.

The proximal end 28 of the dilator 12 comprises a dilator hub 20 fixedly connected to the dilator 12 such as by an adhesive, ultrasonic bonding, insert molding or another method known to those skilled in the art. The dilator hub 20 includes a proximal end 23 having a male threaded portion 25, and at its distal end a lip 22 having a bottom face 24. The threaded portion 25 of the proximal end 23 of the dilator 12 may be used as a temporary fitting for any apparatus (not shown) that may be required to be attached to the dilator 12. The bottom face 24 is flush around its circumference. A distal portion 29 of the dilator hub 20 also includes external male threads 30 that are located between the lip 22 and the stem 26.

The sheath 14 is preferably constructed of high-density polyethylene, low-density polyethylene or polytetrafluoroethylene. The sheath hub 40 is preferably constructed of high-density polyethylene or polypropylene. The dilator is preferably constructed of high-density polyethylene, low-density polyethylene or polypropylene. The dilator hub is preferably constructed of high-density polyethylene or polypropylene.

Referring to FIG. 1, the dilator and sheath assembly 10 comprises the dilator 12 and the sheath 14 wherein the dilator 12 and sheath 14 are releasably locked to each other. When in the releasably locked position, the dilator 12 is positioned inside of the sheath 14 so that the distal tip 36 of the dilator protrudes from the distal end 56 of the sheath 14. Referring back to FIG. 3, the male threads 30 of the dilator hub 20 are engagable with the female threads 53 of the sheath hub 40. The releasably locking engagement between the dilator 12 and the sheath 14 further serves to prevent blood from flowing between the dilator 12 and the sheath 14. In the preferred embodiment, the external male threads 30 on the dilator hub 20 are engagable with the female threads 53 on the sheath hub 40 for approximately one-quarter turn (90°) in the clockwise direction about the longitudinal axis "L" of the dilator 12. However, those skilled in the art will recognize that the engagement between the dilator 12 and the sheath 14 may take any number of turns in either the clockwise or counterclockwise direction.

The female threaded portion 53 of the sheath hub 40 may also be mated to a capping device (not shown) to prevent blood loss through the sheath 14 while not requiring the inserting physician to apply his or her thumb to block the opening 51 in the top flush surface 50 during the period between removal of the dilator 12 and the insertion of the catheter into the sheath 14. If the transition time is short, the use of the thumb is preferred, but if there were some delay between the removal of the dilator 12 and the insertion of the catheter, a capping device would allow the inserting physician to reduce blood loss and contamination through the sheath 14. With this configuration the capping device utilizes the female threaded 53 portion on the sheath hub 14 and is releasably lockable and unlockable using the same unlocking process utilized in removing the dilator 12.

Figure 5:
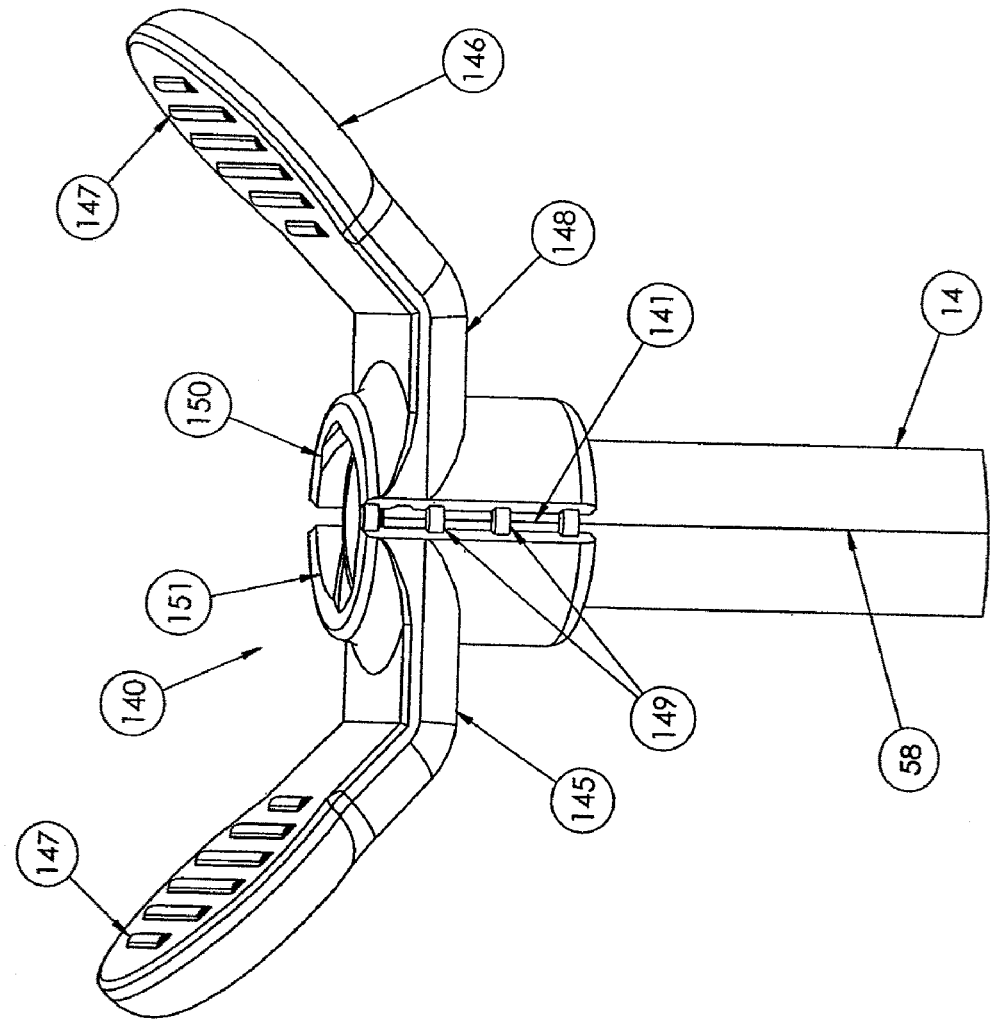
FIG. 5 is a perspective view of a portion of a sheath in accordance with an alternate embodiment of the present invention.

One alternate embodiment of a sheath hub 140, as shown in FIG. 5, is a hub 140 comprising two separate hub portions 145, 148 fixedly connected to the sheath 14, wherein each of a first hub portion 145 and second hub portion 148 is connected to the other by one or more webbings 149. There are spaces 141 between the hub portions 145, 148. These spaces 141 are spanned by the webbings 149 that connect the first and second hub portions 145, 148. The two hub portions 145, 148, when connected by the webbings 149 and bonded to the sheath 14, serve as a singular sheath hub 140. When combined, the two hub portions 145, 148 have all of the features that the sheath hub 40 (FIG. 3) comprises, including a releasably locking mechanism to mate to the counterpart located on the dilator 12, and a flush top surface 150 to assist in the prevention of blood loss through the sheath 14. The webbing 149 that connects the two hub portions 145 may be located in one or more places between the two portions of the sheath hub 140. The webbing 149 and the spaces 141 between the two hub portions 145 of the sheath hub 140 are disposed in the same plane that contains the one or more tear seams 58 along the sheath 14. The features of the sheath hub 140 are virtually identical to those mentioned in the paragraphs above, with respect to the sheath hub 40, with one notable difference being that there are small spaces 141 between the two hub portions 145, 148 of the sheath hub 140 and webbing 149 connecting those portions. The two hub portions 145, 148 have generally semicircular inner surfaces and, when the two hub portions 145, 148 are fixedly connected to the sheath 14, the two hub portions 145, 148 are the functional equivalent of the flush surface 50 and the female threaded portion 53 included in the hub 40 (FIG. 3). The two hub portions 145, 148 also serve as the proximal end 52 of the sheath 14. The space 141 replaces the opposing reveals 48 as a weak point in the sheath hub 40, which assists in splitting the sheath hub 40. The webbing 149 connecting the two hub portions 145, 148 has strength less than that of the rest of the sheath hub 140. This localized decrease in strength allows for splitting of the sheath hub 140 into two separate sheath hub portions 145, 148. The webbing 149 is disposed along a proximal opening 151 so that a flush top surface 150 is intact. This sheath hub 140 configuration can be manufactured utilizing a unitary construction.

A preferred method for using the dilator and sheath assembly 10 will now be described. The method will be described with reference to the dilator and sheath assembly 10 as described above, however, it should be understood that alternative devices described above or which are capable of accomplishing the same steps may also be used. As shown in FIG. 1, the dilator and sheath assembly 10 has an original configuration, wherein the dilator 12 is disposed inside of the sheath 14 and the dilator 12 and sheath 14 are releasably locked to each other. In this position, the distal tip 36 of the dilator 12 protrudes from the distal end 33 of the sheath 14. Also, in this position, the dilator 12 and sheath 14 are releasably locked by the male threads 30 and female threads 53 disposed on the dilator hub 20 and sheath hub 40 respectively.

Figure 6:
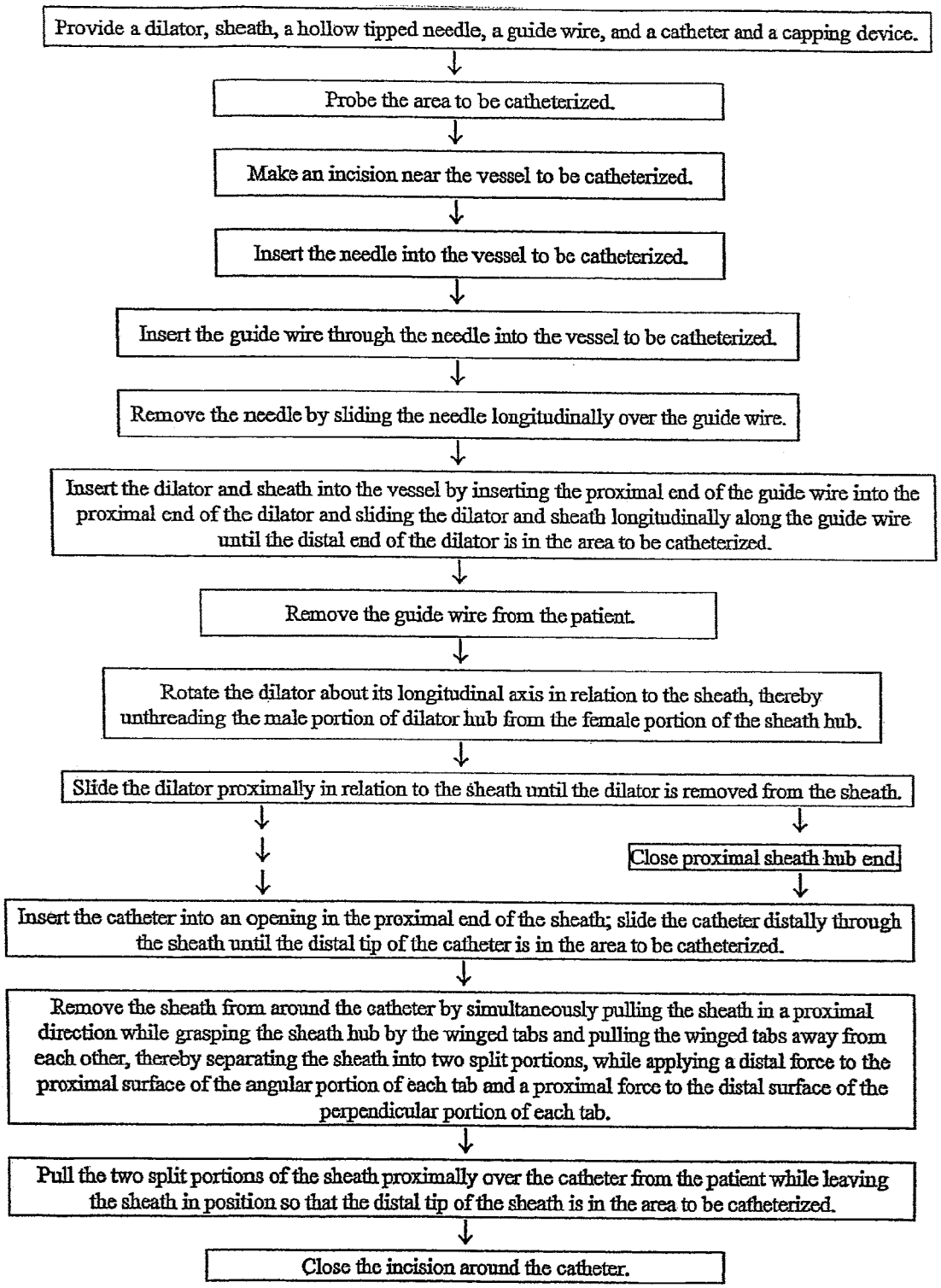
FIG. 6 is a flowchart describing the procedure of catheter insertion utilizing the present invention.

Referring to the flowchart of FIG. 6, during insertion of a catheter into the patient, the dilator and sheath assembly 10 is inserted into a vessel to be catheterized (not shown) so that the distal tip 36 of the dilator 12 is in the area to be catheterized. This is done by first probing the area to be catheterized to find the desired vessel. Next, in accordance with the Seldinger technique, an incision is made near the vessel and a thin, hollow tipped needle (not shown) is inserted through the incision and into the vessel to be catheterized. Once the hollow tip of the needle is in the vessel to be catheterized, a thin guidewire (not shown) is passed through the needle into the vessel. The guidewire is inserted into the vessel so that the distal end of the guidewire is near the desired location to be catheterized. With the guidewire in place, the needle is removed. The dilator and sheath assembly 10 is inserted over the guidewire, with the guidewire being inserted through the hollow passageway 31 of the dilator 12. In this procedure, the proximal end of the guidewire is inserted into the hollow passageway 31, beginning in the distal tip 36 of the dilator 12, and the dilator and sheath assembly 10 is slid along the guidewire in a distal direction until the distal tip 36 of the dilator 12 is in the area to be catheterized. With the dilator and sheath assembly 10 in place, the guidewire is removed by pulling the guidewire in a proximal direction through the dilator 12 and leaving the dilator and sheath assembly 10 in place.

Once the dilator and sheath assembly 10 is in place, the dilator 12 is removed from the sheath 14. The dilator 12 is rotated around its longitudinal axis in a counterclockwise direction in relation to the sheath 14 until the dilator 12 is released from the sheath 14. The dilator 12 is then released from the sheath 14 when the male threads 30 of the dilator hub 20 are no longer engaged to the female threads 53 of the sheath hub 40. Once the dilator 12 is released from the sheath 14, the dilator 12 is pulled in a proximal direction in relation to the sheath 14 until the distal tip 36 of the dilator 12 is clear of the top flush surface 50 of the proximal end 52 of the sheath hub 40. With the dilator 12 clear of the sheath 14, there is now a hollow passageway through the sheath 14. In the preferred embodiment, the dilator 12 is rotated approximately 90° in relation to the sheath 14 to release the engagement between the dilator 12 and the sheath 14.

However, if there is an alternative releasably locking device existing in place of the male threads 30 and female threads 53 on the dilator 12 and sheath 14, respectively, the dilator 12 may be released from the sheath 14 using the appropriate method. These alternative methods include but are not limited to snap fit, screw fit, press fit and locking tabs.

Once the dilator 12 is removed from the sheath 14, leaving a hollow passageway through the sheath 14, a catheter (not shown) may be inserted through the sheath 14 into the desired vessel to be catheterized. The distal tip of the catheter is inserted into the proximal opening 51 of the sheath 14 and the catheter is slid distally through the sheath 14 until the distal tip of the catheter is in the desired location inside of the vessel to be catheterized. To reduce or prevent blood leakage through the sheath 14, before the catheter is inserted through the sheath 14, the inserting physician may apply his or her thumb to the flush top surface 50 of the sheath hub 40 to form a seal. Alternatively, the inserting physician may releasably lock a capping device (not shown) into place on the sheath hub 40, utilizing the mating device on the sheath hub 40 and a mating device on the capping device comprising the same features as the mating device on the dilator 12.

With the catheter in place, the sheath 14 can now be removed, leaving only the catheter in the vessel to be catheterized. It is common for the catheter to have some sort of encumbrance such as a hub, an ingrowth cuff, a collar or other fitting in its proximal region that would prevent the sheath 14 from simply being slid over the catheter for removal. The encumbrance could be a cuff, hub, or other fitting. To accommodate removal of the sheath 14 over a catheter with such encumbrances, the sheath 14 may be split longitudinally. The preferred method of removing the sheath 14 according to the present invention is to split the sheath 14 along its longitudinal axis "L" while pulling the sheath 14 proximally out of the patient. The sheath 14 and the sheath hub 40 are split longitudinally into two approximate halves. This method utilizes the tear seams 58 along the sheath 14 and the two opposing reveals 48 located on the sheath hub 40.

Figure 7:
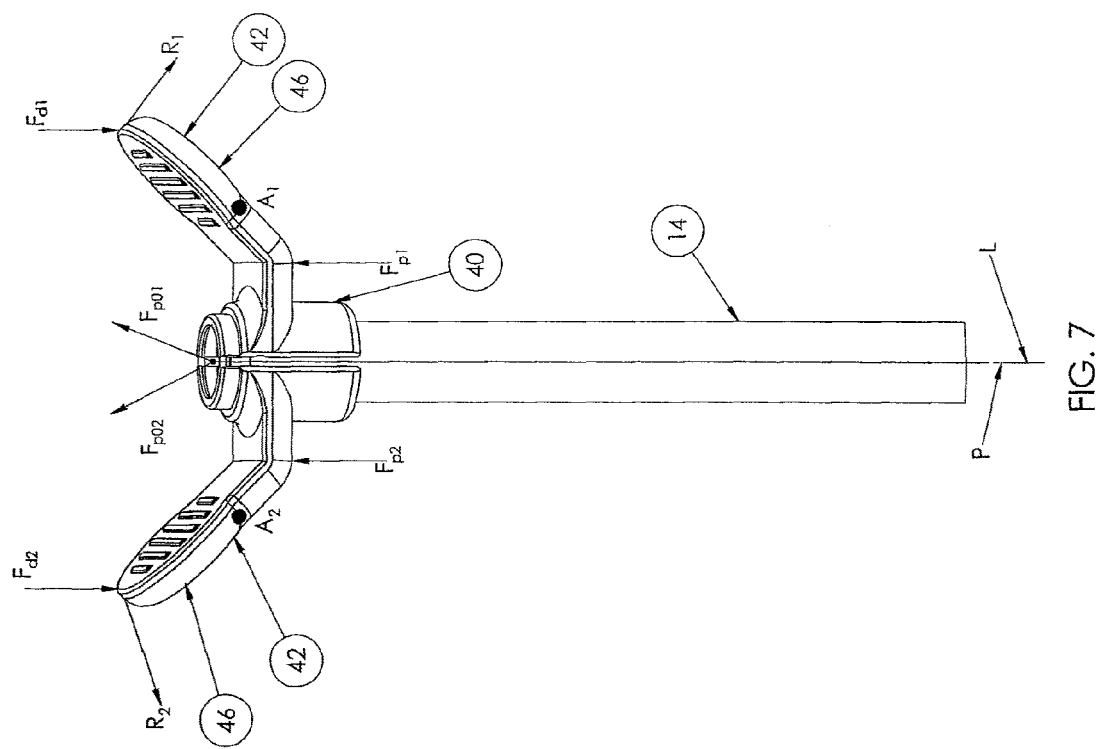
FIG. 7 is a diagram showing a preferable force application used to longitudinally split the sheath upon removal.

Referring to FIG. 7, the sheath 14 is split by grasping the two winged tabs 42 and applying a downward or distal force $F_{d1}$, $F_{d2}$ to the proximal or top surface of the angled portion 46 of each of the winged tabs 42 while applying a proximal force $F_{p1}$, $F_{p2}$ to the distal surface of each of the winged tabs 42 at a place on each tab that is closer to the longitudinal axis "L" of the sheath 14 than the point on each winged tab 42 where the downward force is applied. Preferably, the inserting physician will grasp the tabs 42 by placing his or her thumb on the top of the angled portion 46 of each winged tab 42 and sliding his or her index finger under each tab 42. The distal force $F_{d1}$, $F_{d2}$ is applied with the inserting physician's thumbs and the proximal force $F_{p1}$, $F_{p2}$ is applied with the inserting physician's index finger. This application of conflicting forces $F_{d1}$, $F_{d2}$ and $F_{p1}$, $F_{p2}$ in strategic positions creates a couple which utilizes the winged tab 42 design of the present invention to assist the inserting physician in splitting the sheath hub 40 and the sheath 14. The inserting physician creates moments around two points, which are located directly between the application points of the distal and proximal forces $F_{d1}$, $F_{d2}$ and $F_{p1}$, $F_{p2}$, thereby creating a rotation of the winged tabs 42 along lines $R_1$ and $R_2$ which forces the sheath hub 40 to split in the along the plane containing the opposing reveals 48 of the sheath hub 40 and the tear seams 58 of the sheath 14. Essentially, the winged tabs 42 of the sheath hub 40 are used as levers that pull apart and upward (proximally) on the center of the sheath hub 40. This is accomplished by using the point where the proximal force $F_{p1}$, $F_{p2}$ is applied to the bottom of each winged tab 42 as a fulcrum and applying a distal force $F_{d1}$, $F_{d2}$ to a point on the proximal surface of the angled portion 46 of each winged tab 42. Because of the two conflicting forces $F_{d1}$, $F_{d2}$ and $F_{p1}$, $F_{p2}$ being applied to each of the winged tabs 42, the natural reaction is for the sheath hub 40 to split in the along the plane "P" containing the opposing reveals 48 of the sheath hub 40 and the tear seams 58 of the sheath 14. The splitting of the sheath 14 and the sheath hub 40 allows the winged tabs 42 to each rotate about an axis, approximately located at A1, A2, created by the conflicting distal and proximal forces $F_{d1}$, $F_{d2}$ and $F_{p1}$, $F_{p2}$ and located between the application points of the forces $F_{d1}$, $F_{d2}$ and $F_{p1}$, $F_{p2}$. The approximate direction of rotation is denoted by R1 and R2 in FIG. 7. This design allows the inserting physician to apply distal forces $F_{d1}$, $F_{d2}$ to the outside of each of the winged tabs 42 and proximal forces $F_{p1}$, $F_{p2}$ at points closer to the longitudinal axis "L" of the sheath 14 to achieve resulting proximal and outward forces $F_{PO1}$, $F_{PO2}$ on the center of the sheath hub 40.

The angled design of each of the winged tabs 42 greatly improves the leverage that the inserting physician has while working with the sheath 14. The angled portion 46 of each of the winged tabs 42 assists the inserting physician in maneuvering the sheath 14 into place. The angled portion 46 of the winged tabs 42 also allows the inserting physician to be able to reach under each of the tabs 42 with his or her fingers when the sheath 14 is completely inserted in the body of the patient thereby allowing the inserting physician to place at least one finger under each tab 42 to achieve greater leverage in his or her efforts to split the sheath 14 longitudinally in order to withdraw the sheath 14 while leaving the catheter in place.

This invention is an improvement over the conventional perpendicular tabbed designs because of the leverage that the winged tab 42 design gives the inserting physician during splitting and because the angular portion 46 of the winged tabs 42 allows the inserting physician to place his or her fingers under the tabs 42 with minimal disturbance to the patient. The benefit of the lever and fulcrum style winged tabs 42 over conventional perpendicular tabs is a reduction in the required effort to split the sheath 14, as well as improved ergonomics and a potential reduction in trauma to the patient. The design of the present invention allows the inserting physician to keep his or her hands in a relatively stationary position, in relation to the center of the sheath 14. The present invention allows the inserting physician to split the sheath hub 40 by creating the couple on the first and second winged tabs 42 of the sheath hub 40 without pulling the sheath 14 in two different directions. This reduction in outward forces on the sheath 14 greatly reduces the chance that the two halves of the split sheath 14 will stretch the incision made in the flesh of the patient.

Preferably, while applying the forces $F_{d1}$, $F_{d2}$ and $F_{p1}$, $F_{p2}$ necessary to split the sheath 14 as described above, the inserting physician will also be moving his or her hands in a proximal direction to bring the two approximate halves of the split sheath 14 toward him or herself. This combination of forces will allow the inserting physician to split the sheath 14 as he or she is pulling it from the patient's body, thereby avoiding any encumbrances on the catheter while leaving the portion of the sheath 14 that is still in the patient's body intact. Gradually as more of the sheath 14 is removed from the patient's body, it is preferable for the inserting physician to move his or her hands slightly away from each other to allow the entire length of the sheath 14 to split and avoid any encumbrances on the catheter. This curvilinear translation of the proximal ends of the two approximate halves, proximally and away from each other, allows the sheath 14 to be slid proximally over the catheter while spreading out enough to clear the catheter's proximal obstacles. This process best accomplishes the goal of removing the sheath 14 from around the catheter while leaving the catheter in place when all of the steps mentioned, from grasping the winged tabs 42 of the sheath hub 40 to pulling the tabs 42 away from each other, are done simultaneously in a fluid motion so as to smoothly remove the sheath 14 from around the catheter. Once the sheath 14 is in place and the catheter is removed, the incision is then closed around the catheter according to procedures known to those skilled in the art.

Figure 8:
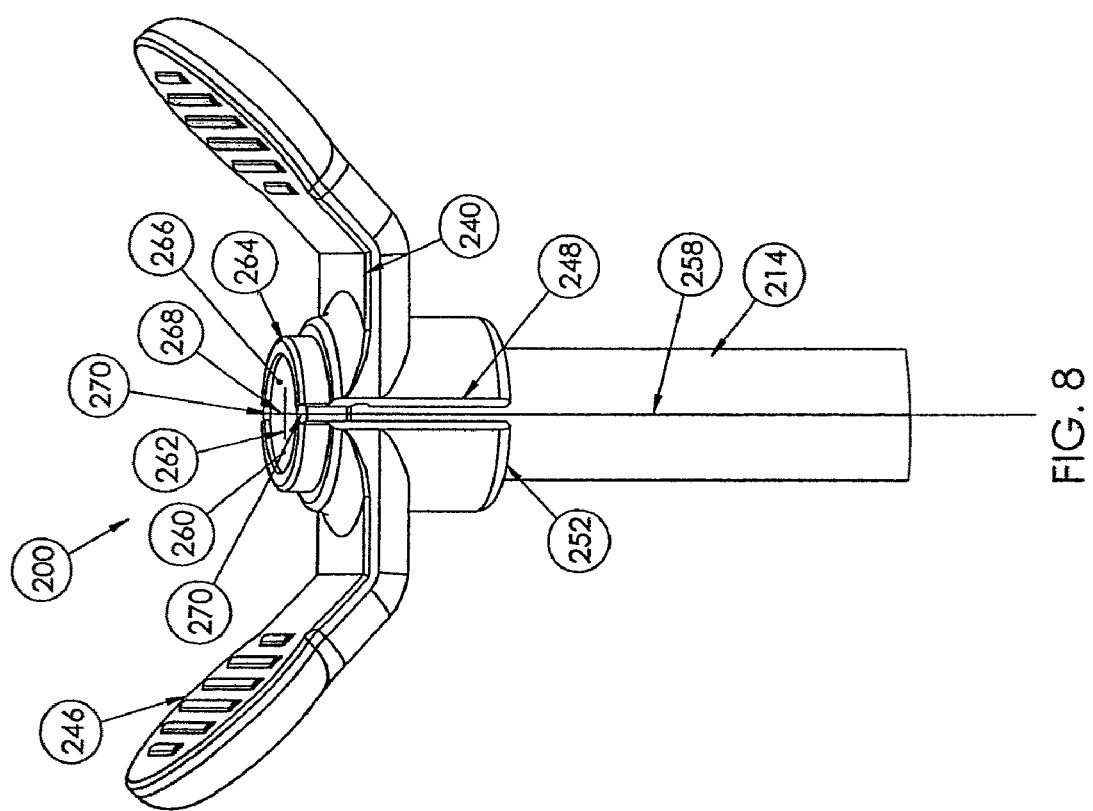
FIG. 8 is a perspective view of a portion of a sheath, in accordance with an alternate embodiment of the present invention.
Figure 8A:
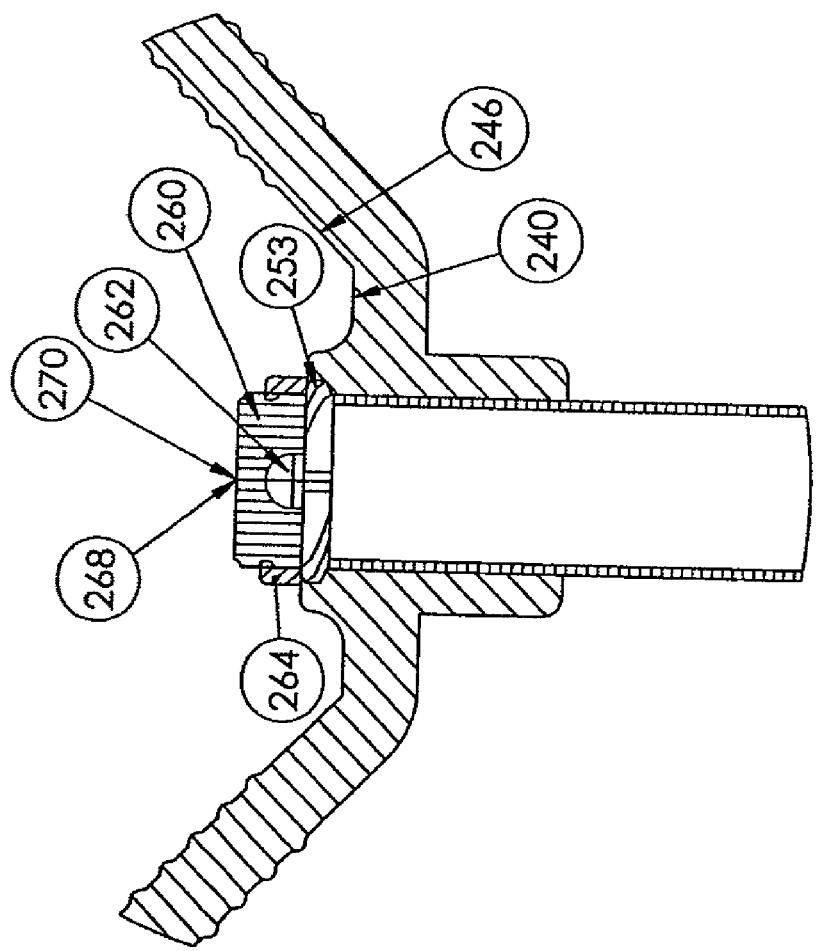
FIG. 8a is a cross-sectional view of the portion of a sheath shown in FIG. 8.

An alternative sheath assembly 200 of the present invention, having a valve 260 located at a proximal end 252 of a sheath 214, is shown in FIGS. 8 and 8a. The valve 260 is preferably shaped in the form of a disc having a diameter that is generally similar to the cross-sectional diameter of the sheath 214. The valve 260 has a longitudinal slit 262 that facilitates the insertion of objects such as a dilator, catheter or syringe (not shown) through the sheath 214 while closing when the inserted object is removed. The valve 260 also seals around the inserted object to prevent blood loss, contamination or the introduction of air into the bloodstream while an object such as a guidewire, dilator or catheter is inserted through the sheath 214. Although the opening in the valve 260 shown in this embodiment is a slit 262, it is known to those skilled in the art that the opening in the valve 260 may be of any shape that will accommodate the insertion of objects such as a dilator, catheter or syringe (not shown) therethrough, such as a cross, or an intersection of any number of slits that share a common center which is preferably aligned with the longitudinal axis of the sheath 214. Preferably, the valve 260 is constructed of silicone, however, those skilled in the art will recognize that the valve 260 may be constructed out of any material that is sufficiently resilient to accommodate the objects inserted therethrough and return to a closed position.

The valve 260 is located at the proximal end 252 of the sheath 214 and is preferably held into place by being bonded to the sheath hub 240 or secured by a cap 264. While FIG. 8. shows a valve 260 that is secured into place by a cap, those skilled in the art will recognize that the valve may be secured directly to the sheath 214 or the sheath hub 240. The cap 264 is preferably constructed of the same material as the sheath hub 240 and fixedly attached to the sheath hub 240 through ultrasonic welding or other suitable means. The cap 264 may also be snap fit onto the hub 240. While FIG. 8 shows a cap 264 that is one piece, those skilled in the art will recognize that the cap 264 may be constructed using more than one piece.

The sheath 214 is generally similar to the sheath 14, described above. Likewise, the sheath hub 240 is generally similar to the sheath hub 40 described above. Female threads 253 are located within the sheath hub 240 distally of the valve 260, similar to the threads 53 shown in FIGS. 2 and 3. A proximal surface 266 of the valve 260 contains a notch 268. The notch 268 crosses the proximal surface 266 and preferably is aligned with two diametrically opposed reveals 248 located on the sheath hub 240. Like the embodiment of a dilator sheath assembly 10 shown in FIGS. 1-4, the diametrically opposed reveals 248 shown in FIG. 8 are preferably aligned with tear seams 258 that run longitudinally along the sheath 214. The cap 264 also contains recesses 270 that are aligned with the reveals 248 of the sheath hub 240 and the notch 268 of the valve 260. Together, the notch 268 of the valve 260, the reveals 248, 270 of the sheath hub 240 and the cap 264 and the tear seams 258 of the sheath 214 will facilitate the longitudinal splitting of the assembly 200 when forces are applied to the tabs 246 in the manner described in FIG. 7.

Figure 9:
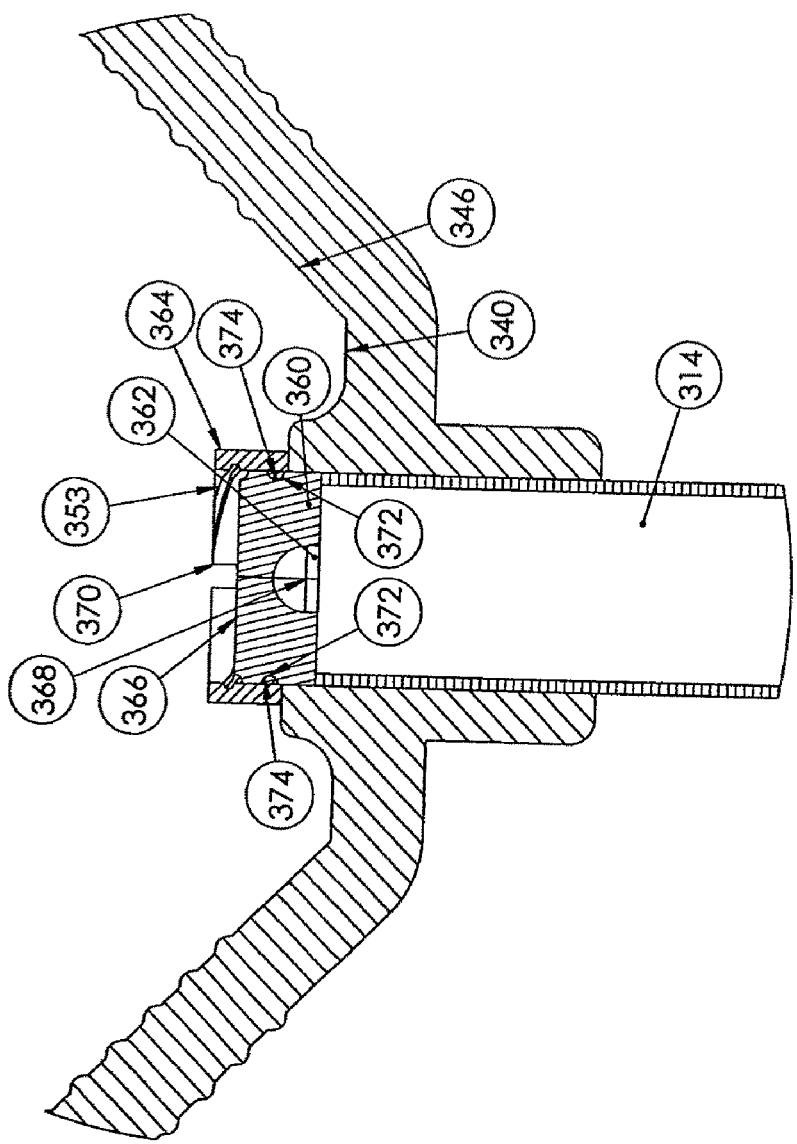
FIG. 9 is a cross-sectional view of a portion of a sheath, in accordance with an alternate embodiment of the present invention.

FIG. 9 shows another alternative embodiment of a sheath assembly 300. The assembly 300 of FIG. 9 is similar to the assembly 200 of FIG. 8; however, in the assembly 300 shown in FIG. 9, a valve 360 is located distally of female threads 353. In this configuration, the female threads 353 are disposed on a cap 364 that is bonded to a sheath hub 340. Like the assembly 200, the assembly 300 is also constructed to facilitate longitudinal splitting when forces are applied to tabs in the manner described in FIG. 7. Referring back to FIG. 9, a notch 368 is disposed across a proximal surface 366 of the valve 360. The notch 368 is aligned with a recess 370 in the cap 364. Although not shown, the notch 368 and the recess 370 are aligned with reveals and tear seams in the hub 340 and sheath 314 respectively. The circumferential surface of the valve 360 may have retaining grooves 372 notched in the surface towards the center of the valve 360. During assembly, the retaining grooves 372 are aligned with retaining protrusions 374 that extend radially inward from the inner surface of the cap 364.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as defined in the claims.

What is claimed is:

1. A dilator and sheath assembly comprising:
   a) a dilator having:
      1) an elongated dilator stem having a proximal dilator end; and
      2) a dilator hub fixedly connected to the proximal dilator end, wherein the dilator hub includes a locking portion at a distal portion thereof; and
   b) a sheath having:
      1) an elongated tubular portion having a proximal sheath end, a distal sheath end, and a longitudinal axis extending between the proximal sheath end and the distal sheath end, wherein the tubular portion is sized to frictionally retain the dilator stem;
      2) at least one tear seam extending in a plane between the proximal sheath end and the distal sheath end;
      3) a sheath hub fixedly connected to the proximal sheath end, wherein the sheath hub includes an elongated tubular portion having a proximal portion, a mating locking portion recessed within the proximal end of the sheath; and
      4) a valve assembled to the sheath hub proximal of the proximal sheath end, wherein the locking portion of the dilator hub and the mating locking portion of the sheath provide a releasably locking engagement between the dilator and the sheath.

2. The dilator and sheath assembly according to claim 1, wherein the at least one tear seam comprises two tear seams located in the plane, wherein the plane longitudinally bisects the sheath.

3. The dilator and sheath assembly according to claim 2, wherein the sheath hub further comprises two opposing reveals along its elongated tubular portion and disposed parallel to the longitudinal axis of the tubular portion, and wherein the opposing reveals are located in the plane including the at least one tear seam.

4. The dilator and sheath assembly according to claim 2, wherein the sheath hub further comprises two opposing reveals along its elongated tubular portion and disposed parallel to the longitudinal axis of the tubular portion, wherein the opposing reveals are located in the plane including the two tear seams, and wherein the valve is disposed proximally of the mating locking portion of the sheath hub.

5. The dilator and sheath assembly according to claim 4, wherein the valve includes defined therein a longitudinal slit aligned with reveals and tear seams to facilitate the longitudinal splitting of the assembly.

6. The dilator and sheath assembly according to claim 2, wherein the sheath hub further comprises two opposing reveals along its elongated tubular portion and disposed parallel to the longitudinal axis of the tubular portion, wherein the opposing reveals are located in the plane including the two tear seams, and wherein the valve is disposed distally of the mating locking portion of the sheath hub, and a cap is secured onto the proximal end of sheath hub and contains the locking portion, the cap securely maintaining in place the valve.

7. The dilator and sheath assembly according to claim 6, wherein the cap includes therewithin protrusions disposed within a corresponding annular retaining grooves around the circumferential surface of the valve to further assure securing the valve within the sheath hub.

8. The dilator and sheath assembly according to claim 6, wherein the at least one tear seam comprises two tear seams located in the plane, wherein the plane longitudinally bisects the sheath, and wherein the sheath hub further comprises two opposing reveals along its elongated tubular portion and disposed parallel to the longitudinal axis of the tubular portion, wherein the opposing reveals are located in the plane including the two tear seams, and wherein the cap contains a recess wherein the valve further includes a notch in the proximal surface thereof, both the recess and notch being aligned with reveals and tear seams to facilitate the longitudinal splitting of the assembly.

9. The dilator and sheath assembly according to claim 1, wherein the locking portion of the dilator hub further comprises one of a male and a female thread and the mating locking portion of the sheath hub comprises the other of the male and female thread so as to mate to the dilator hub to provide a releasably locking engagement between the dilator and the sheath.

10. The dilator and sheath assembly according to claim 1, wherein the sheath hub comprises a flush surface at the proximal portion thereof, wherein the flush surface is perpendicular to the longitudinal axis of the tubular portion, wherein the flush surface is generally flat around an entire circumference of an opening in the sheath hub, and wherein the opening defines a proximal end of the tubular portion, all such that the flush surface enables manual contact therewith sufficient to prevent blood loss during use.

11. The dilator and sheath assembly according to claim 1, wherein the sheath hub comprises two opposing winged tabs, wherein each winged tab includes a perpendicular portion and an angled portion, wherein the perpendicular portion extends laterally from the sheath hub in a plane perpendicular to the longitudinal axis of the tubular portion, and wherein the angled winged tab portion extends in a proximal direction from the perpendicular portion and has a proximal surface, wherein an angle between the proximal surface of the perpendicular portion and that of the angled portion is between approximately 90° and approximately 179°.

12. The dilator and sheath assembly according to claim 11, wherein the angle is between approximately 130° and approximately 140°.

13. A dilator and sheath assembly comprising:
   a) a dilator having an elongated dilator stem, a proximal dilator end and a dilator hub fixedly connected to the proximal dilator end, wherein the dilator hub includes a locking portion at a distal portion thereof; and b) a sheath having:
  (i) a proximal sheath end, a distal sheath end and an elongated tubular portion having a longitudinal axis extending between the proximal sheath end and the distal sheath end;
  (ii) two tear seams extending along the tubular portion between the proximal sheath end and the distal sheath end, wherein the two tear seams are located on opposite sides of the sheath and are in a plane containing the longitudinal axis of the sheath;
  (iii) first and second opposing sheath hub portions, wherein each of the first and second sheath hub portions comprise an inverted semicircular edge fixedly connected to the sheath, whereby the first and second sheath hub portions define an elongated tubular hub portion that generally encircles the tubular sheath and whereby there are small spaces along the tubular hub portion and between the first and second sheath hub portions, wherein the spaces between the first and second sheath hub portions are aligned with the two tear seams on the sheath; wherein the first and second sheath hub portions comprise first and second locking portions at a proximal end thereof and recessed within the sheath, whereby the first and second locking portions form a circular locking portion forming the proximal end of the sheath, and whereby the locking portion is matable with the locking portion of the dilator hub to provide a releasably locking engagement between the dilator and the sheath; and
  (iv) a valve assembled to the sheath hub and located between the proximal sheath hub end and the distal sheath hub end proximal of the proximal end of the elongated tubular sheath portion.

14. The dilator and sheath assembly according to claim 13, wherein the locking portion of the dilator hub includes one of a male and a female thread and the mating locking portion of the sheath hub includes the other of the male and female thread so as to mate to the dilator to provide a releasably locking device to attach the dilator to the sheath.

15. The dilator and sheath assembly according to claim 13, wherein the first and second opposing sheath hub portions are connected to each other on either side of the longitudinal axis by at least one web on opposing sides of the longitudinal axis, wherein the at least one web constitutes a weakened portion in the sheath hub, bonded to the sheath hub portions to form a complete circle around the sheath, wherein the at least one web has a tensile strength less than that of the sheath hub.

16. The dilator and sheath assembly according to claim 15, wherein the at least one web is positioned along a proximal opening in the sheath hub, whereby the at least one web and the two sheath hub portions form a flush top surface, wherein the flush top surface is generally flat, wherein the flush top surface is perpendicular to the longitudinal axis of the sheath, and wherein the flush top surface defines a proximal end in the tubular hub portion, all such that the flush top surface enables manual contact therewith sufficient to prevent blood loss during use.

17. The dilator and sheath assembly according to claim 13, wherein the first and second opposing sheath hub portions are connected on either side of the longitudinal axis by a member on each side, wherein the member is bonded to the hub portions to form a complete circle around the sheath, wherein the member is of a tensile strength less than that of the sheath hub portions so as to assist in the splitting of the sheath and separation of the sheath along the plane containing the axis of the sheath and the two tear seams.

18. The dilator and sheath assembly according to claim 13, wherein the sheath hub further comprises two opposing reveals along its tubular portion and disposed parallel to the longitudinal axis of the tubular portion, wherein the opposing reveals are located in the plane including the two tear seams, and wherein the valve is disposed proximally of the mating locking portion of the sheath hub.

19. The dilator and sheath assembly according to claim 13, wherein the valve includes defined therein a longitudinal slit aligned with reveals and tear seams to facilitate the longitudinal splitting of the assembly.

20. The dilator and sheath assembly according to claim 13, wherein the sheath hub further comprises two opposing reveals along its tubular portion and disposed parallel to the longitudinal axis of the tubular portion, wherein the opposing reveals are located in the plane including the two tear seams, wherein the valve is disposed distally of the mating threaded portion of the sheath hub, and a cap is secured onto the proximal end of sheath hub and contains the threaded portion, the cap securely maintaining in place the valve.

21. The dilator and sheath assembly according to claim 20, wherein the cap includes therewithin protrusions disposed within a corresponding annular retaining grooves around the circumferential surface of the valve to further assure securing the valve within the sheath hub.

22. The dilator and sheath assembly according to claim 20, wherein the cap contains a recess wherein the valve further includes a notch in the proximal surface thereof, both the recess and notch being aligned with reveals and tear seams to facilitate the longitudinal splitting of the assembly.

* * * * *